US009804130B2

(12) United States Patent
Tat et al.

(10) Patent No.: US 9,804,130 B2
(45) Date of Patent: Oct. 31, 2017

(54) SYSTEM AND METHOD FOR PROVIDING SIMULATED ULTRASOUND POROSITY WAVEFORMS

(71) Applicant: The Boeing Company, Chicago, IL (US)

(72) Inventors: Hong H. Tat, Redmond, WA (US); Gary E. Georgeson, Tacoma, WA (US); Richard H. Bossi, Renton, WA (US)

(73) Assignee: The Boeing Company, Chicago, IL (US)

( * ) Notice: Subject to any disclaimer, the term of this patent is extended or adjusted under 35 U.S.C. 154(b) by 256 days.

(21) Appl. No.: 14/707,403

(22) Filed: May 8, 2015

(65) Prior Publication Data

US 2017/0016861 A1    Jan. 19, 2017

(51) Int. Cl.
| | | |
|---|---|---|
| G01N 29/11 | (2006.01) | |
| G01N 15/08 | (2006.01) | |
| G01N 29/44 | (2006.01) | |

(52) U.S. Cl.
CPC .............. G01N 29/11 (2013.01); G01N 15/08 (2013.01); G01N 15/088 (2013.01); G01N 29/4427 (2013.01); *G01N 2291/015* (2013.01); *G01N 2291/0231* (2013.01)

(58) Field of Classification Search
CPC ...... G01N 29/11; G01N 29/46; G01N 29/043; G01N 29/0645; G01N 29/2475; G01N 29/265; G01N 29/4418; G01N 29/2418; G01N 29/449; G01N 29/30; G01N 27/902; G01N 15/08; G01N 15/088; G01N 19/4427
See application file for complete search history.

(56) References Cited

U.S. PATENT DOCUMENTS

| | | | | |
|---|---|---|---|---|
| 4,538,462 A | * | 9/1985 | Hartog .................... | G01N 19/04 73/577 |
| 6,234,025 B1 | * | 5/2001 | Gieske .................. | G01N 29/221 73/629 |
| 6,684,701 B2 | * | 2/2004 | Dubois .................. | G01N 29/11 73/579 |
| 6,843,130 B2 | * | 1/2005 | Georgeson ............. | G01N 29/11 73/600 |

(Continued)

*Primary Examiner* — Helen Kwok
(74) *Attorney, Agent, or Firm* — Economou Silfin LLP; John S. Economou

(57) ABSTRACT

A system and method is disclosed for generating ultrasound results having a simulated level of porosity for a composite. Data for a set of composite coupons having different levels of porosity is obtained. An attenuation distribution function is fit to a back wall signal generated from the data for each coupon and a library of echo patterns based on such data is created. An interpolated attenuation distribution function is calculated based on an interpolation of two stored attenuation distribution functions having the closest porosity values to the selected level. A main attenuation distribution function value is assigned to one portion of a selected region in a zero porosity coupon and attenuation distribution functions values within a predetermined percentage of the main attenuation distribution function are assigned to other portions of the region. Waveforms associated with the portions are modified based on such values and selected echo patterns from the library.

20 Claims, 13 Drawing Sheets

(56) References Cited

U.S. PATENT DOCUMENTS

| | | | |
|---|---|---|---|
| 7,389,693 B2* | 6/2008 | Reed | G01N 15/088 |
| | | | 73/597 |
| 7,434,468 B2* | 10/2008 | Puckett | G01N 29/11 |
| | | | 73/1.86 |
| 7,478,569 B2 | 1/2009 | Bossi et al. | |
| 7,584,062 B1 | 9/2009 | Tat et al. | |
| 7,617,714 B2* | 11/2009 | Engelbart | G01N 29/043 |
| | | | 73/1.03 |
| 7,617,730 B2 | 11/2009 | Georgeson | |
| 7,694,546 B2* | 4/2010 | Engelbart | G01N 29/30 |
| | | | 73/1.82 |
| 7,823,451 B2 | 11/2010 | Sarr | |
| 8,332,165 B1 | 12/2012 | Tat et al. | |
| 8,894,787 B2* | 11/2014 | Boe | B32B 38/10 |
| | | | 156/155 |
| 2004/0261530 A1* | 12/2004 | Meier | G01N 15/088 |
| | | | 73/579 |
| 2007/0101815 A1* | 5/2007 | Kollgaard | G01N 29/30 |
| | | | 73/618 |
| 2008/0125653 A1* | 5/2008 | Antich | A61B 8/0875 |
| | | | 600/438 |
| 2008/0148854 A1* | 6/2008 | Georgeson | G01N 29/11 |
| | | | 73/599 |
| 2009/0025479 A1* | 1/2009 | Kollgaard | G01N 29/04 |
| | | | 73/599 |
| 2009/0044627 A1* | 2/2009 | Brady | G01N 29/2406 |
| | | | 73/643 |
| 2010/0024559 A1 | 2/2010 | Bossi et al. | |
| 2011/0218743 A1* | 9/2011 | Smith | G01N 29/11 |
| | | | 702/56 |
| 2014/0333758 A1 | 11/2014 | Wu et al. | |
| 2014/0346405 A1* | 11/2014 | Ferguson | G01N 29/30 |
| | | | 252/408.1 |
| 2016/0320353 A1* | 11/2016 | Biwa | G01N 29/46 |

* cited by examiner

SYSTEM AND METHOD FOR PROVIDING SIMULATED ULTRASOUND POROSITY WAVEFORMS

GOVERNMENT LICENSE RIGHTS

This invention was made with Government support under A7117-300-01-12-CA1510 awarded by the Department of Defense. The government has certain rights in this invention.

FIELD

This disclosure relates generally to a system and method for providing simulated ultrasound porosity waveforms for use in porosity testing of a composite material.

BACKGROUND

As the use of composite materials increases, the development of advanced nondestructive testing techniques for composite materials has also increased. Ultrasonic quantitative nondestructive testing techniques for composite materials can provide important information on manufacturing quality, material strength and useful lifetime. Porosity is one type of defect in composites that can be difficult to detect and measure. Porosity is typically caused by internal spaces (voids) within the composite material. Ultrasonic nondestructive testing techniques require a porosity reference standard to calibrate the measurements for a composite component provided by the ultrasonic testing equipment. It has been found, however, that the process of fabricating porosity reference standards can be complicated, time consuming and expensive. This process typically requires large numbers of composite coupons to be fabricated and many testing sites or samples to be taken for porosity measurements, and still will only result in a finite number of coupons. Selection of testing sites is essentially random, which requires iterations of coupon fabrication and porosity measurements to form reference standards representing a range of percent porosities.

Accordingly, there is a need for an improved way to generate porosity reference standards for use in ultrasonic nondestructive testing of composite materials.

SUMMARY

In one aspect, a method for generating simulated ultrasound test results having a selected level of porosity for a particular material under test. A region of ultrasound test results for a coupon among a set of coupons of a selected material is selected, the selected region within a region of porosity below a minimum predetermined threshold, the selected region for adding a predetermined amount of simulated porosity, the region of the ultrasound test results comprising a plurality of ultrasound waveforms. A main attenuation distribution function based on an interpolation of two of a set of stored attenuation distribution functions for the set of coupons is calculated, one of the two stored attenuation distribution functions for a coupon in the set of coupons having a porosity less than the predetermined amount of simulated porosity and the other of the two stored attenuation distribution functions for a coupon in the set of coupons having a porosity greater than predetermined amount of simulated porosity. A main attenuation value is assigned to one portion of the selected region based on the main attenuation distribution function. The ultrasound waveforms associated with the one portion of the selected region are modified based on the main attenuation value and a selected one echo pattern of a library of echo patterns generated from ultrasound test results for the set of coupons. Attenuation values within a predetermined percentage of the main attenuation value are assigned to other portions of the selected region. The ultrasound waveforms associated with the other portions of the selected region are modified based on the attenuation values within a predetermined percentage of the main attenuation value and a selected one echo pattern of the library of echo patterns. Finally, the modified ultrasound waveforms are stored in a computer memory as simulated ultrasound waveforms for the predetermined amount of simulated porosity.

In one further aspect, a two-dimensional smoothing of the modified ultrasound waveforms may be performed prior to the storing step. In another further aspect, the ultrasound waveforms may be modified by extracting a front-wall pulse portion of the ultrasound waveform and storing the extracted front-wall pulse portion in a memory, modifying the selected echo pattern by setting a back-wall pulse portion in the selected echo pattern and any portion after the back-wall pulse portion in the selected echo pattern to zero, convolving the extracted front-wall pulse portion with the modified selected echo pattern to create an interim ultrasound signal, attenuating the stored front-wall pulse portion by the associated attenuation value and time-shifting the attenuated front-wall pulse portion to be a simulated back-wall pulse portion, and adding the simulated back-wall pulse portion to the interim ultrasound signal to create a simulated ultrasound waveform. Still further, prior to modifying the selected echo pattern, the location and amplitude of echoes in the selected echo pattern may be randomly perturbated. In yet another further aspect, the simulated ultrasound waveforms may be forwarded to a nondestructive testing system for use as a porosity reference standard for the selected level of porosity. Yet further, the selected region may be divided into a number of randomly-sized sub-regions, a main attenuation distribution function is calculated for each sub-region, and a main attenuation value and assigning attenuation values having values within a predetermined percentage of the main attenuation value are assigned for each sub-region. Finally, the selected region may be divided into a number of randomly-sized sub-regions by selecting boxes of randomly-selected width and length to fill the selected region.

In a second aspect, a system for generating simulated ultrasound test results having a selected level of porosity for a particular material under test. An ultrasound test system is configured to perform ultrasound testing on a set of coupons for the particular material under test, each of the coupons having a different level of porosity and/or thickness, to generate ultrasound test data for each coupon. A processor is configured to fit a distribution function to a back wall attenuation signal for each coupon in the set of the coupons and to store the fitted distribution function in a memory as an attenuation distribution function, the back wall attenuation signal generated from the ultrasound test data for each coupon. The processor is configured to create, from the ultrasound test data, a library of echo patterns for each coupon of unique porosity and thickness in the set of coupons and to store the library of echo patterns in a memory. The processor is configured to select a region of ultrasound test results of a coupon having a region of zero porosity for adding a predetermined amount of simulated porosity. The processor is configured to calculate a main attenuation distribution function based on an interpolation of two of the stored attenuation distribution functions, one of the two stored attenuation distribution functions for a coupon in the set of coupons having a porosity less than the predetermined amount of simulated porosity and the other of the two stored attenuation distribution functions for a coupon in the set of coupons having a porosity greater than the predetermined amount of simulated porosity. The processor is configured to assign a main attenuation value to one portion of the selected region based on the main attenuation distribution function and to assign attenuation values within a predetermined percentage of the main attenuation value to other portions of the selected region. The processor is configured to modify the ultrasound waveforms associated with the one portion of the selected region based on the main attenuation value and a selected one echo pattern of the library of echo patterns. The processor is configured to modify the ultrasound waveforms associated with the other portions of the selected region based on the attenuation values within a predetermined percentage of the main attenuation value and a selected one echo pattern of the library of echo patterns. The processor is configured to store the simulated ultrasound waveforms in a memory as simulated ultrasound waveforms for the selected level of porosity.

In one further embodiment, the processor may be further configured to perform a two-dimensional smoothing of the modified ultrasound waveforms prior to storing the simulated ultrasound waveforms in memory. In another further embodiment, the processor may be further configured to modify the ultrasound waveforms by extracting a front-wall pulse portion of the ultrasound waveform and storing the extracted front-wall pulse portion in a memory, to modify the selected echo pattern by setting the back-wall pulse portion in the selected echo pattern and any portion after the back-wall pulse portion in the selected echo pattern to zero, to convolve the extracted front-wall pulse portion with the modified selected echo pattern to create an interim ultrasound signal, to attenuate the stored front-wall pulse portion by the associated attenuation value and time-shifting the attenuated front-wall pulse portion to be a simulated back-wall pulse portion, and to add the simulated back-wall pulse portion to the interim ultrasound signal to create a simulated ultrasound waveform. Further, the processor may be further configured to, prior to modifying the selected echo pattern, perform random perturbation of the location and amplitude of echoes in the selected echo pattern. In another further embodiment, the processor may be further configured to forward the simulated ultrasound waveforms to a nondestructive testing system for use as a porosity reference standard for the selected level of porosity. In yet another further embodiment, the processor may be further configured to divide the selected region into a number of randomly-sized sub-regions, to calculate a main attenuation distribution function for each sub-region, and, for each sub-region, to assign a main attenuation value based on the calculated main attenuation distribution function for that sub-region and to assign attenuation values within a predetermined percentage of the main attenuation value for that sub-region. Still further, the processor may be further configured to divide the selected region into a number of randomly-sized sub-regions by selecting boxes of randomly-selected width and length to fill the selected region.

In a third aspect, a method for generating a set of simulated ultrasound test results having predetermined levels of porosity for a particular material under test. A region of the ultrasound test results for a coupon among a set of coupons of a selected material, the selected region within a region of porosity below a predetermined minimum threshold, the selected region for adding simulated porosity, the region of ultrasound results comprising a plurality of ultrasound waveforms. For each of the predetermined levels of porosity: a main attenuation distribution function is calculated based on an interpolation of two of a set of stored attenuation distribution functions for the set of coupons, one of the two stored attenuation distribution functions for a coupon in the set of coupons having a porosity less than a selected one of the predetermined levels of porosity and the other of the two stored attenuation distribution functions for a coupon in the set of coupons having a porosity greater than the selected one of the predetermined levels of porosity; a main attenuation value is assigned to one portion of the selected region based on the main attenuation distribution function; the ultrasound waveforms associated with the one portion of the selected region are modified based on the main attenuation value and a selected one echo pattern of a library of echo patterns generated from ultrasound test data for the set of coupons; attenuation values within a predetermined percentage of the main attenuation value are assigned to other portions of the selected region; and the ultrasound waveforms associated with the other portions of the selected region are modified based on the attenuation values within a predetermined percentage of the main attenuation value and a selected one echo pattern of the library of echo patterns. Finally, the modified ultrasound waveforms are stored in a computer memory as simulated ultrasound waveforms for the selected one of the predetermined levels of porosity.

The features, functions, and advantages that have been discussed can be achieved independently in various embodiments or may be combined in yet other embodiments, further details of which can be seen with reference to the following description and drawings.

BRIEF DESCRIPTION OF THE DRAWINGS

The following detailed description, given by way of example and not intended to limit the present disclosure solely thereto, will best be understood in conjunction with the accompanying drawings in which.

DETAILED DESCRIPTION

In the present disclosure, like reference numbers refer to like elements throughout the drawings, which illustrate various exemplary embodiments of the present disclosure. The present disclosure describes a system and method used to provide simulated ultrasound test data for composite materials. As one of ordinary skill in the art will readily recognize in view of the present disclosure, the disclosed system and method can be applied to provide simulated ultrasound test data for any material having a varying level of porosity.

Figure 1A:
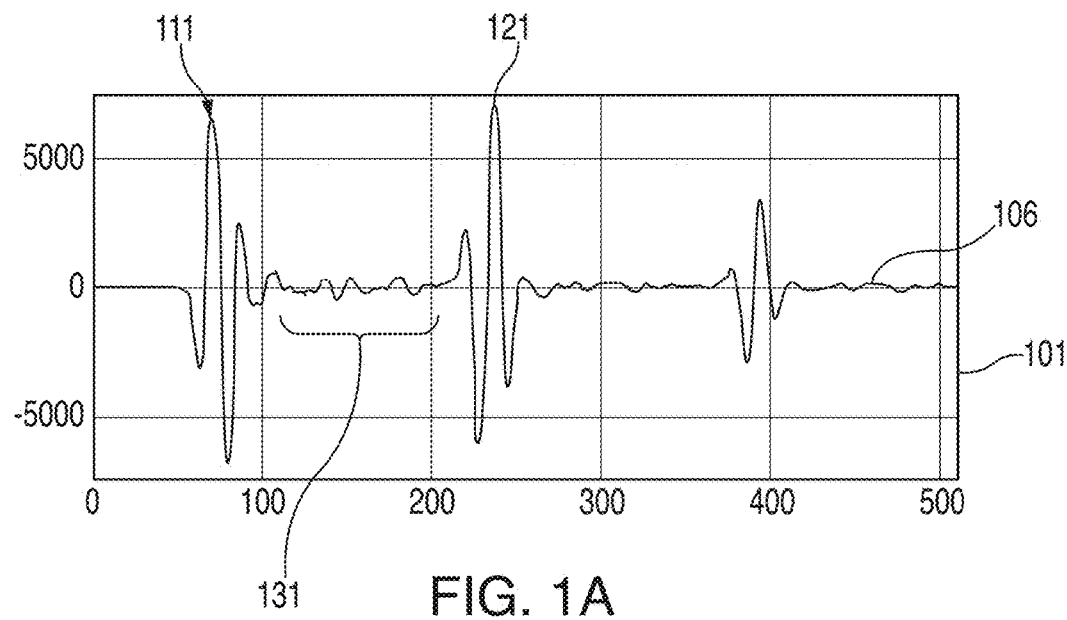
FIGS. 1A, 1B, 1C and 1D are respective A-scan plots of ultrasound testing results of composite coupons having four different levels of porosity.
Figure 1B:
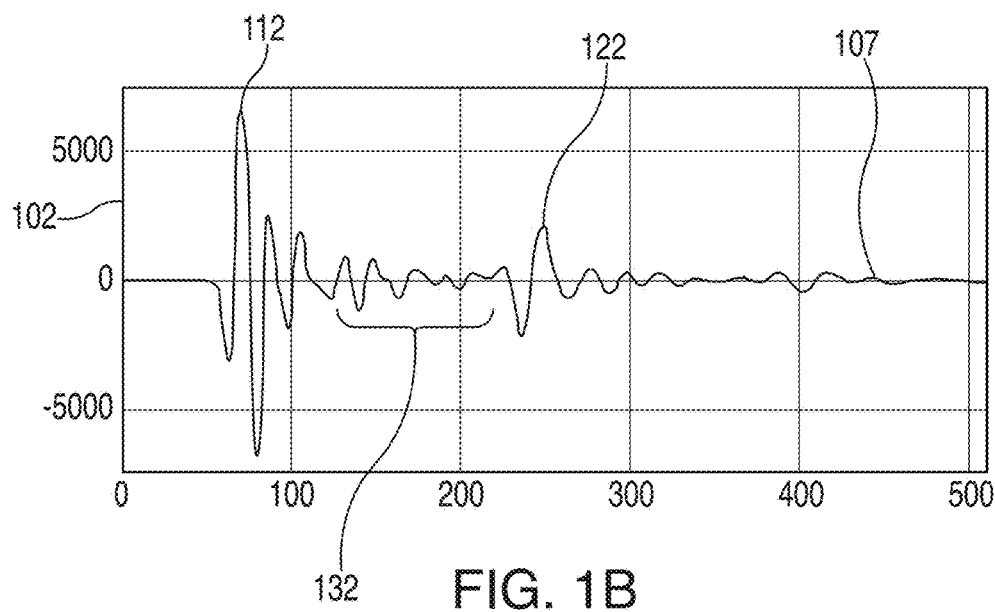
Figure 1C:
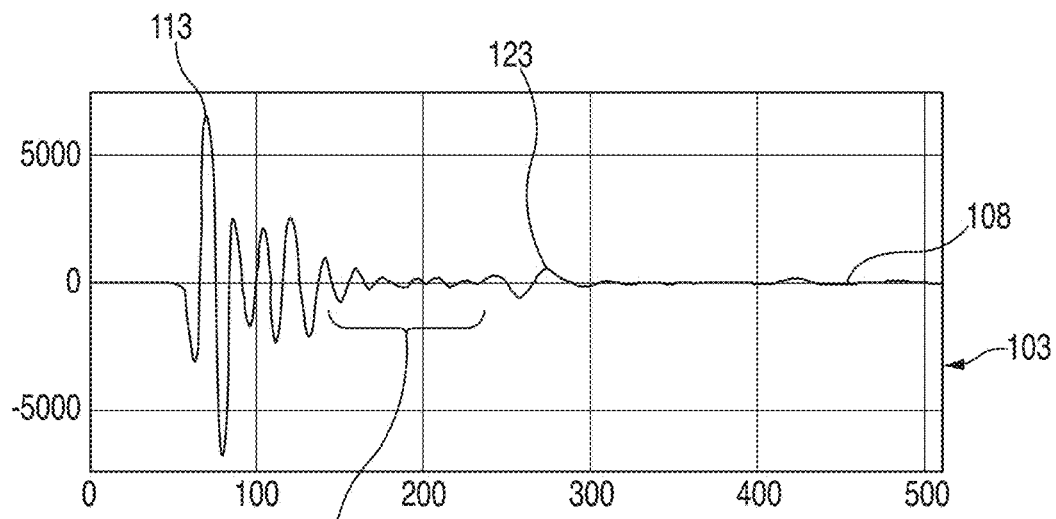
Figure 1D:
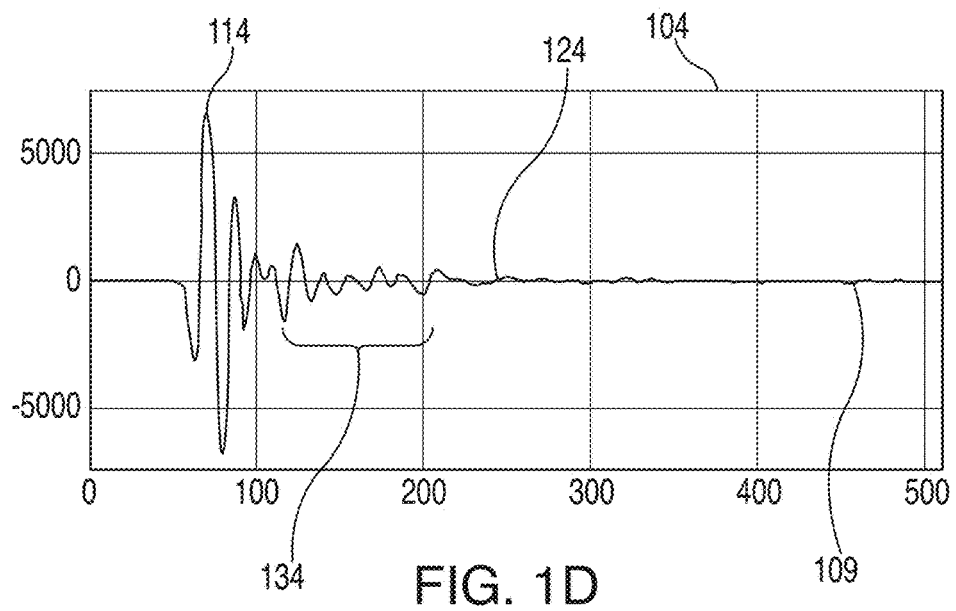

Referring now to FIGS. 1A to 1D, four A-scan plots 101-104 are shown of ultrasonic testing of four respective composite coupons for a particular composite material having four varying levels of porosity, ranging from porosity percent a in plot 101, porosity percent b in plot 102, porosity percent c in plot 103 to porosity percent d in plot 104, where a<b<c<d. As known by those of ordinary skill in the art, an A-scan plot of an ultrasound test shows received ultrasound energy signal as a function of time. In particular, in FIGS. 1A to 1D, the respective ultrasound energy signals 106-109 are shown for the four respective composite coupons. In FIG. 1A, plot 101 shows a first magnitude increase 111 at the front wall of composite coupon under test (i.e., the coupon having the lowest level of porosity) and a second magnitude increase 121 at the back wall of that coupon. As can be seen from plots 102-104 in FIGS. 1B to 1D, respectively, as the porosity increases, the front wall signal levels 112-114 do not change while the back wall signal levels 122-124 decrease. Thus, increased levels of porosity cause increased attenuation of the back wall signal level. Although not shown in FIGS. 1A-1D, increased levels of porosity can also be seen by increased mottling and darker shading of the C-scan plot of the ultrasound test. As known by those of ordinary skill in the art, a C-scan plot of an ultrasound test provides a plan-type view of the location and size of features of the composite part under test. In addition, as seen by the regions 131-134 in plots 101-104, as porosity increases, the waveform tends to include additional signals between the front wall signal points 111-114 and the back wall signal points 121-124 due to internal echoes caused by the porosity. As discussed in more detail below, the system and method disclosed herein provides simulated ultrasound porosity waveforms for any level of porosity of interest during composite nondestructive testing based on these two signal features, changing back wall attenuation and increased internal echo responses.

Figure 2:
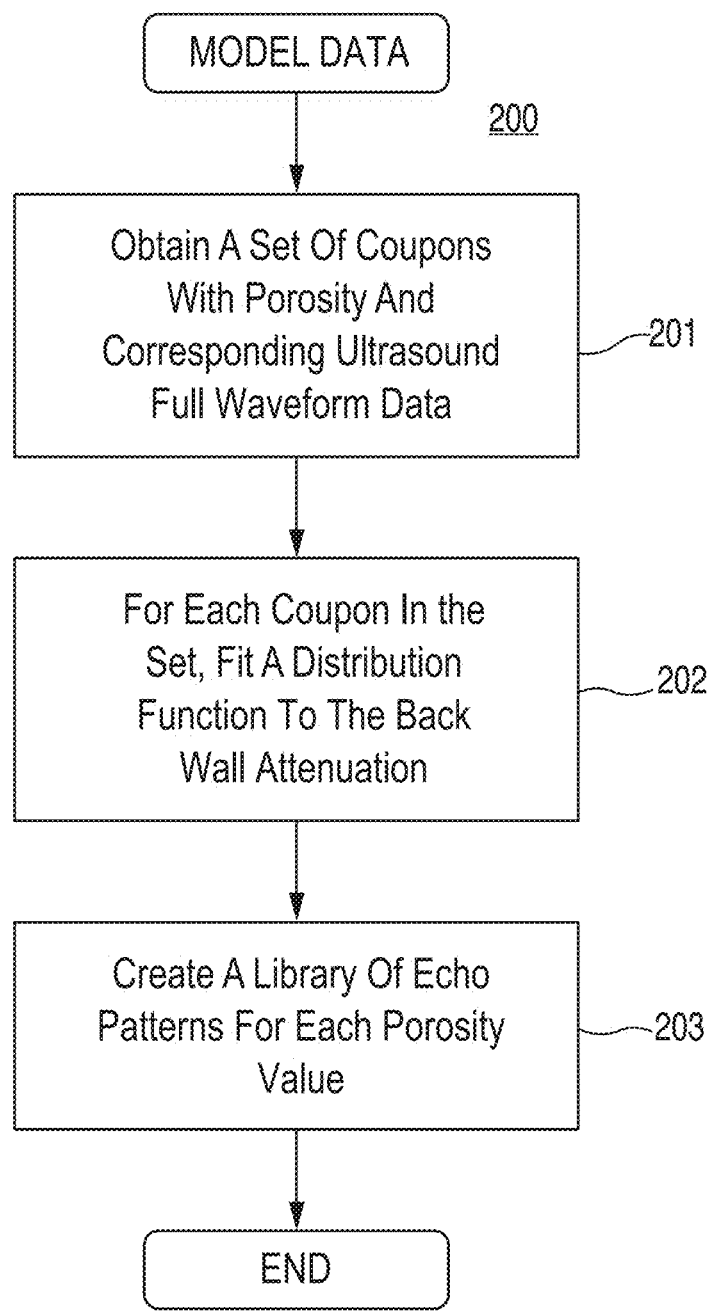
FIG. 2 is a flowchart showing the data modelling steps according to an aspect of the system and method of the present disclosure.

As shown in flowchart 200 in FIG. 2, to provide simulated ultrasound porosity waveforms for a composite material under test, the system and method disclosed herein first models the data for a set of composite coupons. First, a set of composite coupons for a particular composite material is obtained and testing is performed to obtain the ultrasound signal waveforms for that set of composite coupons (step 201). Notably, the composite material under test does not need to be exactly the same as the composite material used for the set of composite coupons. Then, for each coupon in the set, a distribution function is fit to the back wall attenuation signal portion for each coupon (step 202). Finally, a library of echo patterns is created for each porosity value among the set of composite coupons (step 203).

For step 201, ultrasound data is collected within a predetermined region of each composite coupon. In a presently preferred embodiment, the ultrasound data is collected using the system shown in FIG. 12 and described below. For example, when the predetermined region is selected to be a two square inch area of each composite coupon, the testing may preferably require 2500 ultrasonic test data points for each composite coupon. The set of composite coupons may include groups of coupons having a number of different plies. In one example set, the group of composite coupons may include the following thirteen different types of coupons:

TABLE I

|   | Plies | Thickness | Percent Porosity |
|---|---|---|---|
| 1 | 24 | 0.18 | 0.0 |
| 2 | 24 | 0.18 | 2.0 |
| 3 | 24 | 0.18 | 4.0 |
| 4 | 24 | 0.18 | 8.0 |
| 5 | 32 | 0.24 | 0.0 |
| 6 | 32 | 0.24 | 1.0 |
| 7 | 32 | 0.24 | 4.0 |
| 8 | 32 | 0.24 | 8.0 |
| 9 | 48 | 0.36 | 0.0 |
| 10 | 48 | 0.36 | 1.0 |
| 11 | 48 | 0.36 | 3.0 |
| 12 | 48 | 0.36 | 5.0 |
| 13 | 48 | 0.36 | 8.0 |

As evident from Table I above, the relevant parameters for each coupon are the number of plies, the total coupon thickness and the percent porosity.

Figure 3:
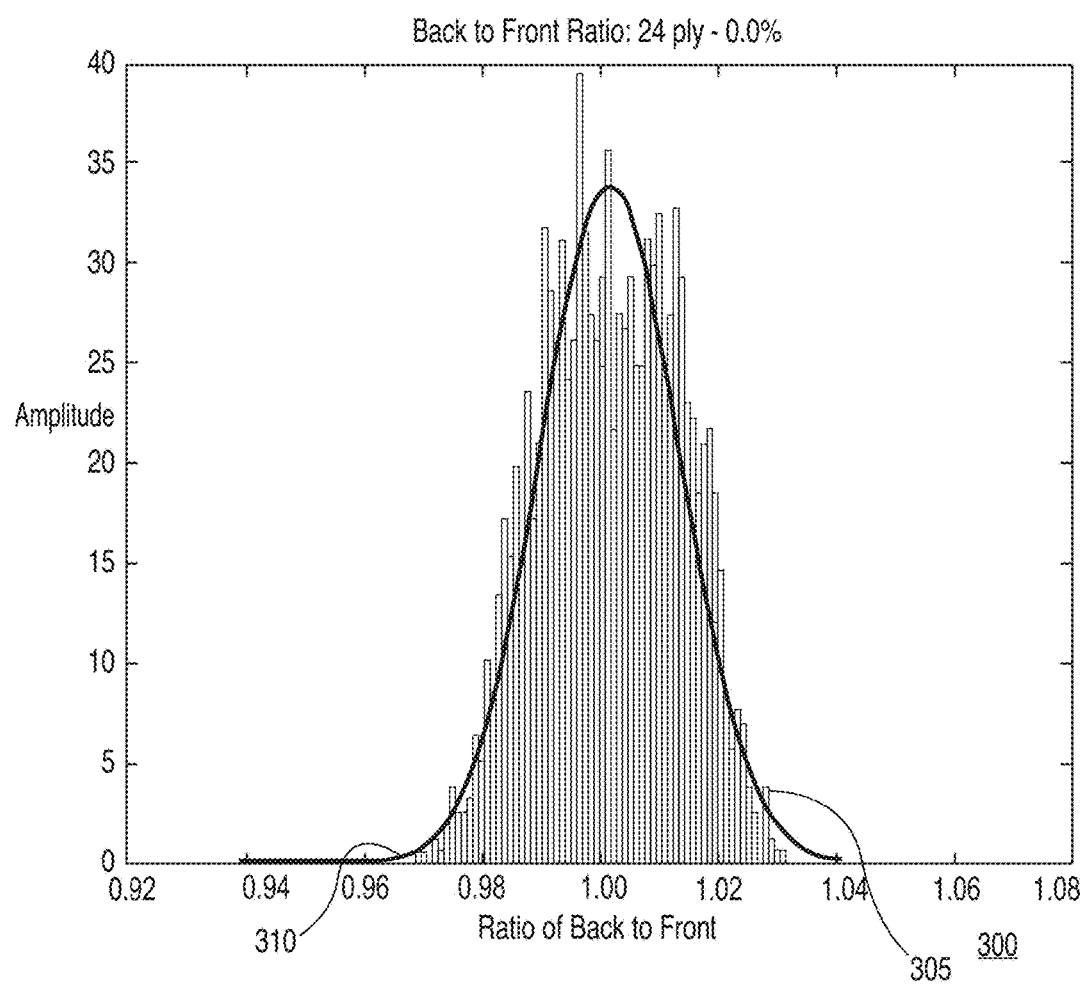
FIG. 3 is a plot showing an attenuation distribution function being fit to ultrasound test data according to an aspect of the system and method of the present disclosure.
Figure 12:
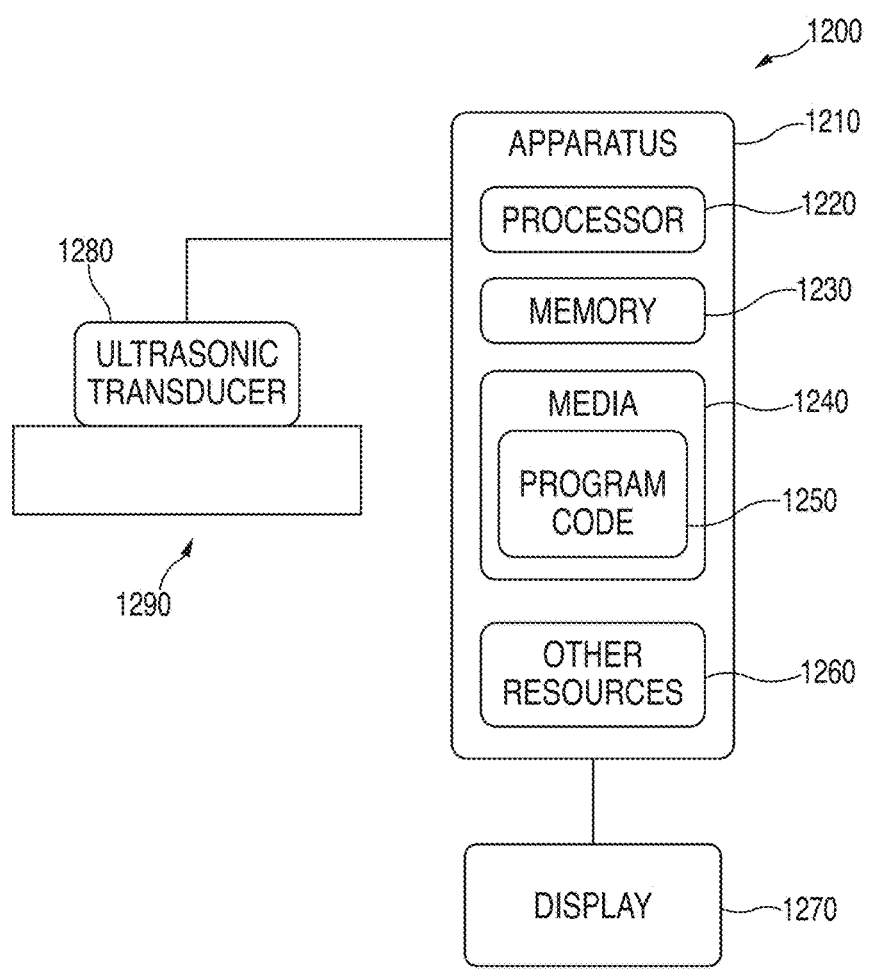
FIG. 12 is a block diagram depicting a system in accordance with an implementation of the present disclosure.

Referring now to FIG. 3, at step 202 a distribution function is fit to the back wall attenuation of the ultrasound waveforms for each composite coupon in the set (preferably step 202 is performed by the system shown in FIG. 12). In one presently preferred embodiment, the following distribution function is used:

$$F(x) = \frac{1}{x\sqrt{2\pi\sigma}} e^{-\frac{(lnx-\mu)^2}{2\sigma^2}}$$

where: x=dependent variable;
μ=mean; and
σ=standard deviation.

In FIG. 3, plot 300 shows the signal amplitude (plotted as a histogram 305) of the ratio of the back wall ultrasound signal (e.g., portion 121 in FIG. 1A) to the front wall ultrasound signal (e.g., portion 111 in FIG. 1A) for all of the data collected for each composite coupon. This ratio is used to determine the attenuation of the ultrasound signal due to porosity based on the set of composite coupons of measured porosity. This ultrasound attenuation is used to identify the level of porosity in a composite. A distribution function 310 is fit to the histogram 305 data, resulting in the distribution function 310 having a mean of 1.0 and a standard deviation of 0.012. This is repeated for each composite coupon in the set. This step provides a set of calculated attenuation distribution functions, each of the calculated attenuation distribution functions corresponding to an associated composite level of porosity in the set.

Figure 4:
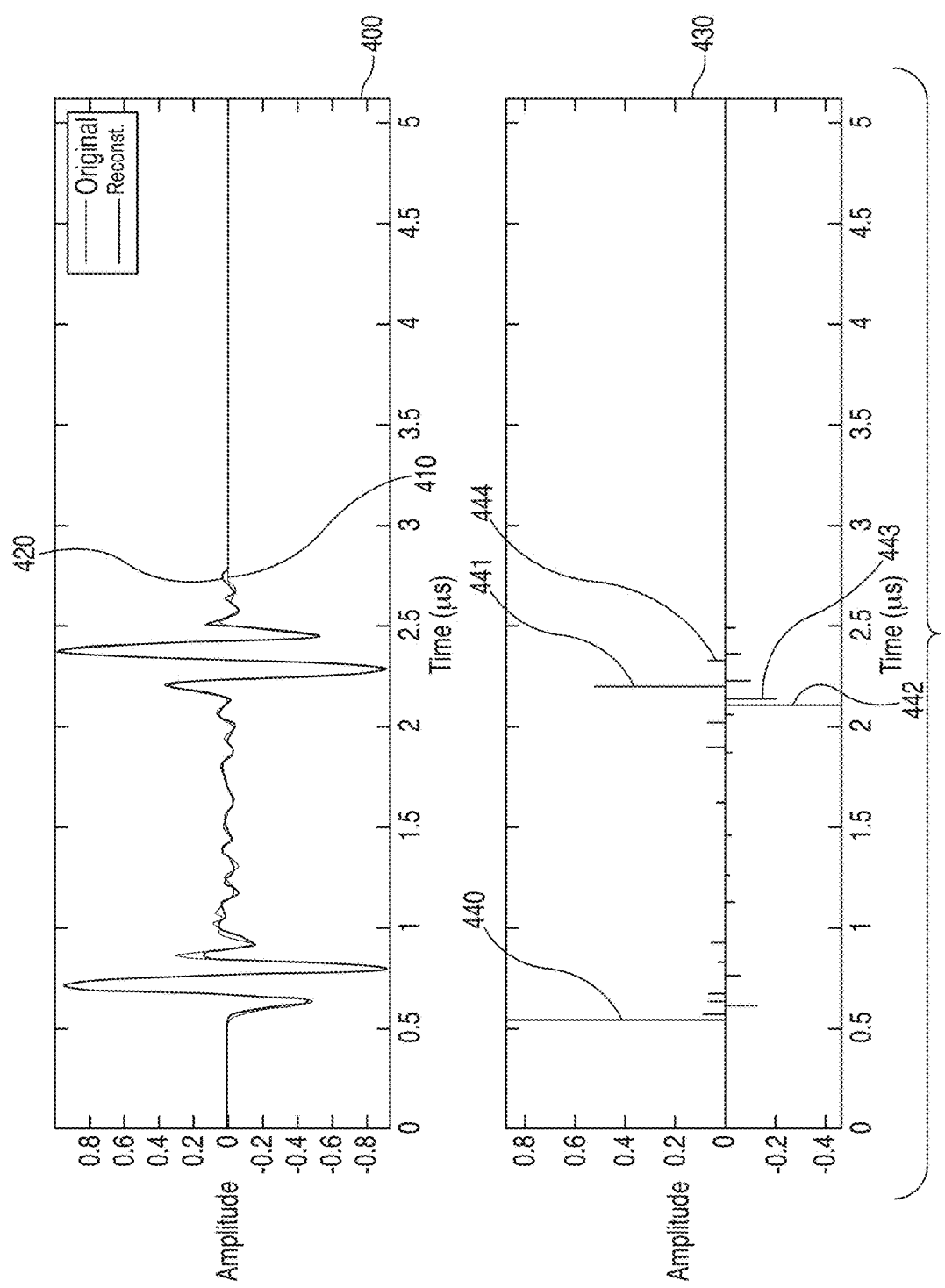
FIG. 4 shows an A-scan plot of ultrasound test data for a ultrasound test sample and an associated plot of echo data in accordance with the system and method of the present disclosure.

Referring now to FIG. 4, at step 203 a library of echo patterns is created for each of the coupons (each porosity value at each thickness) in the set (preferably step 203 is also performed by the system shown in FIG. 12). As discussed above with respect to FIGS. 1A to 1D, as the level of porosity increases in the composite coupons in the set, echoes will increasingly appear between the front wall signal points 111-114 and the back wall signal points 121-124. Since the wavelength of the ultrasound signal may be longer than the distances of interest in a composite (e.g., the distance between the front wall of the composite coupon and the internal spacing causing the porosity—such space also causing the echo, or the distance between plies), each echo may not be readily discernable in the signal waveforms 106-109. U.S. Pat. No. 7,584,062 B1 ("the '062 patent"), which issued on Sep. 1, 2009, discloses a system and method for identifying echoes caused by laminate layers which have a layer thickness shorter than wavelength of the ultrasound signal using compressed sensing (which only identifies echoes having larger significant amplitudes and ignores echoes with smaller amplitudes).

The system and method disclosed herein preferably applies the same methodology as used in the '062 patent to identify the echoes caused by the internal voids that contribute to increased levels of porosity. In particular, a transducer (e.g., a transducer 1280 of FIG. 12 below) provides a stimulus (i.e., outgoing) pulse incident to a multi-layer, laminate material. The outgoing pulse is estimated by the front surface echo (e.g., pulse 111 in FIG. 1A) and is shifted by respective and incremental amounts so that a plurality of pulse vectors are defined. Any number of pulse vectors can be defined in this way such that an incrementally related set of vectors is formed. The pulse vectors are assembled in a chronologically advancing order so as define a matrix "Φ". The ultrasound signal detected by the transducer (e.g., signal 101 in FIG. 1A) after interaction with the laminate material is converted to a corresponding time-domain electrical signal, digitized, and recorded. This resulting recorded, digitized, data is used to define a waveform vector "Y". An automated, computerized search is performed, resulting in a sparse solution vector "X", in accordance with the relationship: Y=Φ*X. The sparse solution vector "X" is the echo pattern of interest. As one of ordinary skill in the art will readily recognize, other techniques may also be used to identify the echo patterns for each of the composite coupons in the set. In FIG. 4, the top plot 400 shows the original ultrasonic energy waveform 410 overlaid by waveform 420 which is reconstructed from the echoes shown in bottom plot 430 (e.g., echoes 440-444 in FIG. 4) which were identified within original ultrasonic energy waveform 410 using the method disclosed in the '062 patent.

Once the data has been collected and modeled using the steps shown in FIG. 2 and discussed above, the system and method disclosed herein next uses such modeled data to provide simulated composite test ultrasound data having any desired preselected level of porosity of interest for composite nondestructive evaluation. In particular, the system and method of the present disclosure alters ultrasonic waveforms taken on a region of a composite coupon without porosity to appear as if the composite did contain a predetermined level of porosity in that region. As discussed herein, this process creates realistic simulated porosity signals and images and is useful for the replacement of physical porosity standards, verification, validation, training purposes, etc. In particular, the system and method of the present disclosure can be used to enhance the development and verification of automated defect recognition (ADR) algorithms, for the replacement of very costly physical porosity standards, for verification and validation of ultrasonic test systems for porosity detection, for verification of ultrasonic inspection procedures, and for training of inspectors for composite inspection. The system and method of the present disclosure provides great cost savings because, based only on the statistics of a limited small set of composite coupons, ultrasound test waveforms can be generated for large arbitrary sets of values of porosity, and can be used as reference standards for many types of nondestructive testing systems.

Figure 5:
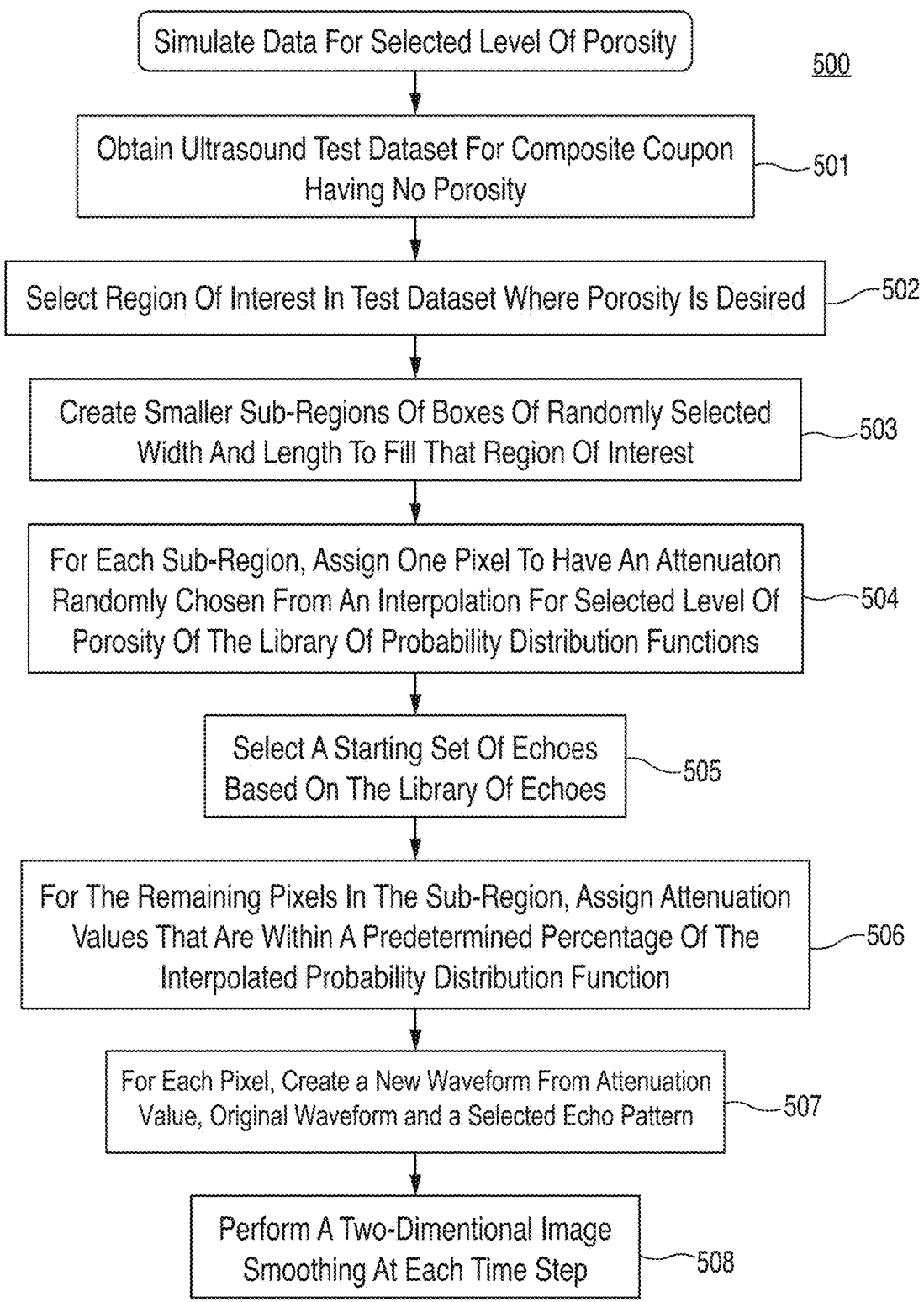
FIG. 5 is a flowchart showing the ultrasound data simulation steps according to an aspect of the system and method of the present disclosure.
Figure 6:
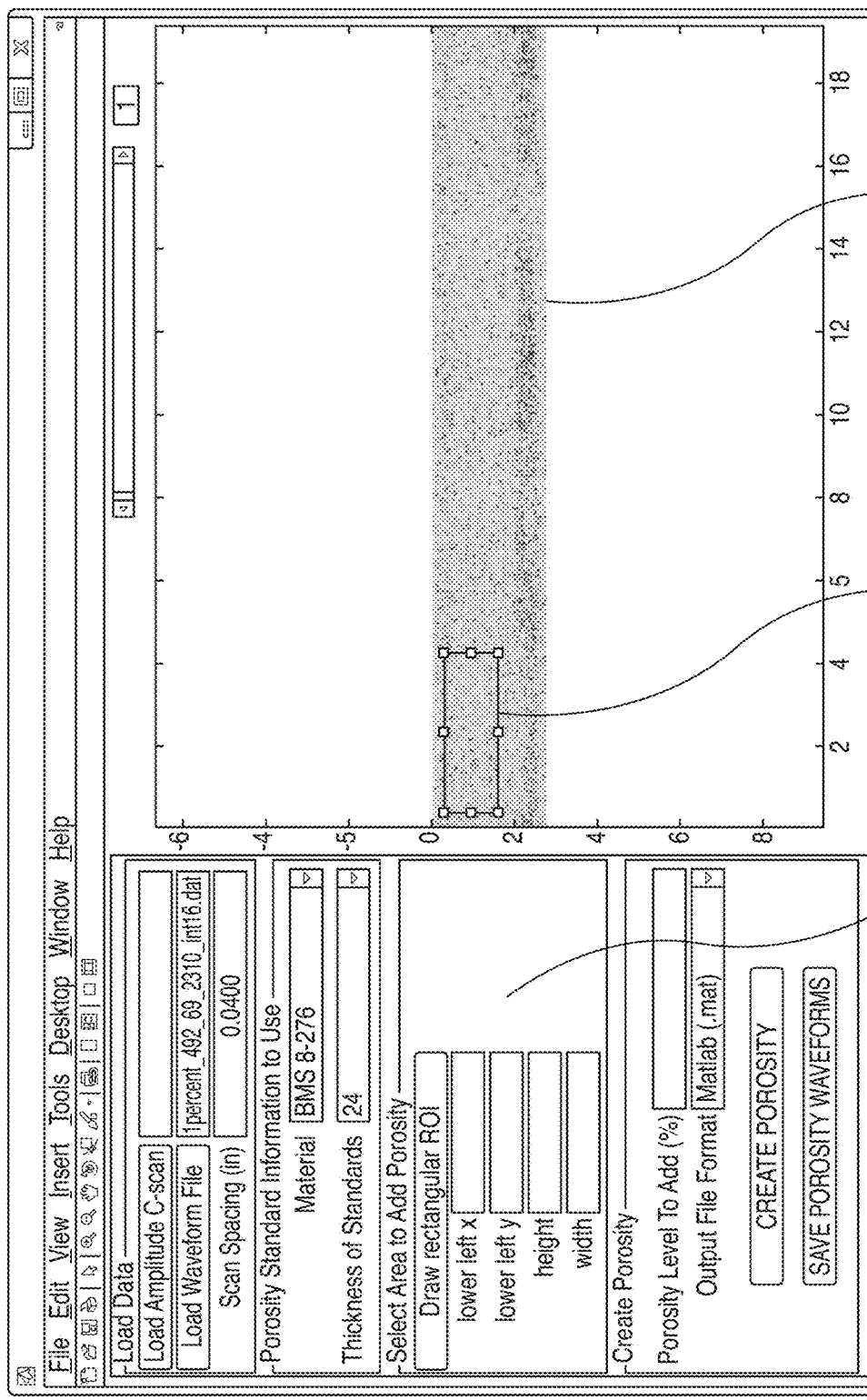
FIG. 6 is a screenshot of an exemplary user interface which may be used as part of the ultrasound data simulation according to an aspect of the system and method of the present disclosure.

Referring now to the flowchart 500 in FIG. 5, the processing required to provide simulated composite test ultrasound data is shown. First, at step 501, an ultrasound test dataset for a composite coupon having no porosity (or a porosity level below a predetermined minimum threshold) is obtained or identified. For example, in the ultrasound testing data shown in Table 1 above, test data for three composite coupons having no porosity is available, and one of the three ultrasound test datasets for the respective composite coupons may be selected. Next, at step 502, a region of interest is selected in the identified test dataset where porosity is to be simulated. This step is shown in more detail in FIG. 6, which shows a C-scan plot 600 for a test data set having no porosity and shows the region 610 selected using the user interface 620. As one of ordinary skill in the art will readily recognize, user interface 620 may be part of the system shown in FIG. 12 or may be part of some other test system adapted to use the test data generated using the system shown in FIG. 12. Once the region of interest 610 is selected, smaller sub-regions of boxes of randomly selected width and length are created to fill the region of interest 610 (step 503).

Figure 7:
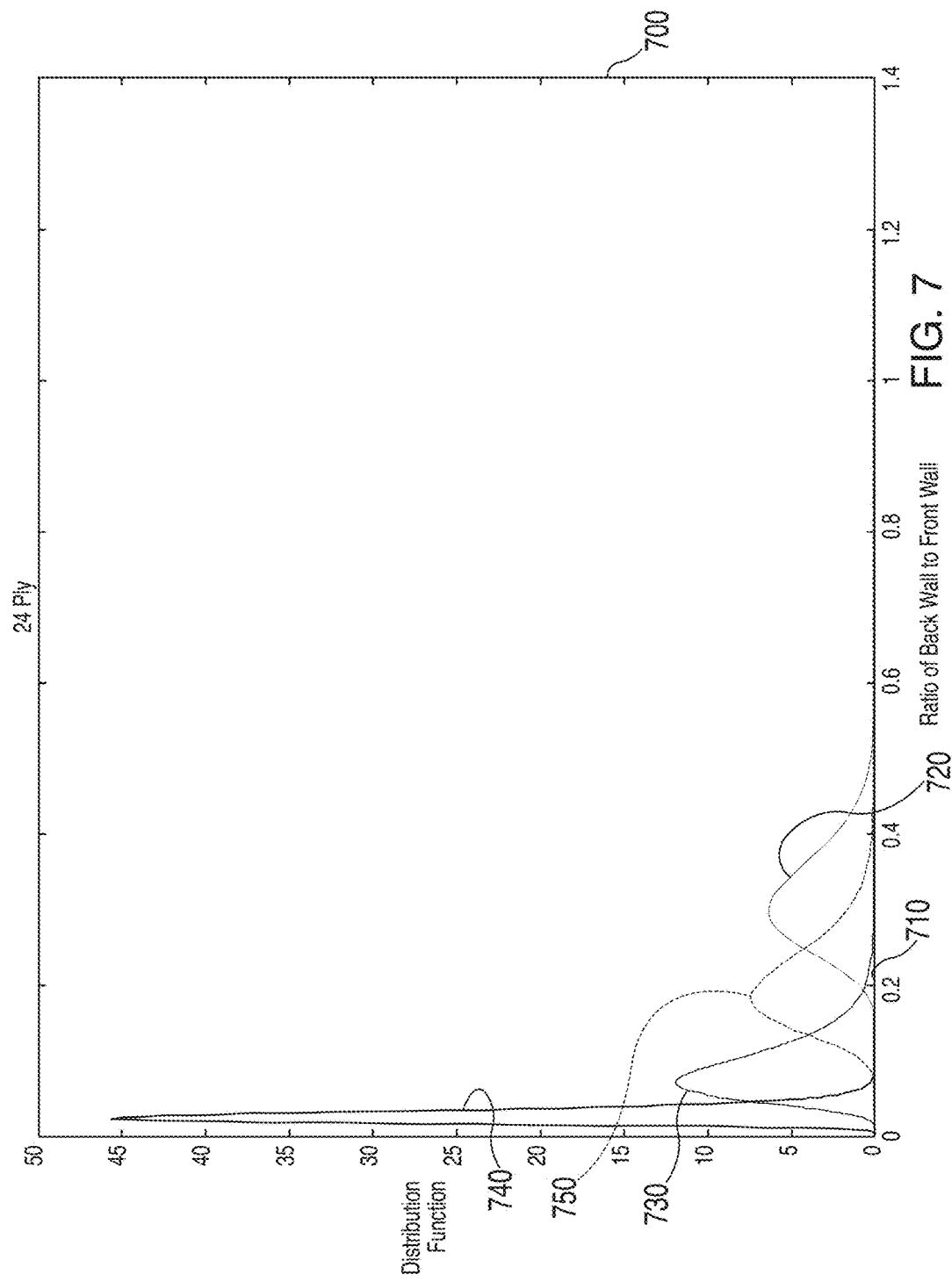
FIG. 7 is a plot that shows the process of interpolating the attenuation distribution function according to an aspect of the system and method of the present disclosure.

Continuing with flowchart 500 in FIG. 5, at step 504 and for each created sub-region, one pixel is assigned to have an attenuation randomly chosen from an interpolation for the preselected level of porosity of the library of distribution functions. In particular, as shown in FIG. 7, ultrasound test data is available for four levels of porosity, zero percent represented by straight line 710, 2.0 percent represented by line 720, 4.0 percent represented by line 730 and 8.0 percent represented by line 740. Thus, for example, when a porosity of 3.0 percent is desired, the two mean and standard deviation values for the attenuation distribution functions for the two adjacent porosity data sets (i.e., 2.0 percent and 4.0 percent) are interpolated to create a new attenuation distribution function represented in FIG. 7 by line 750.

Figure 8:
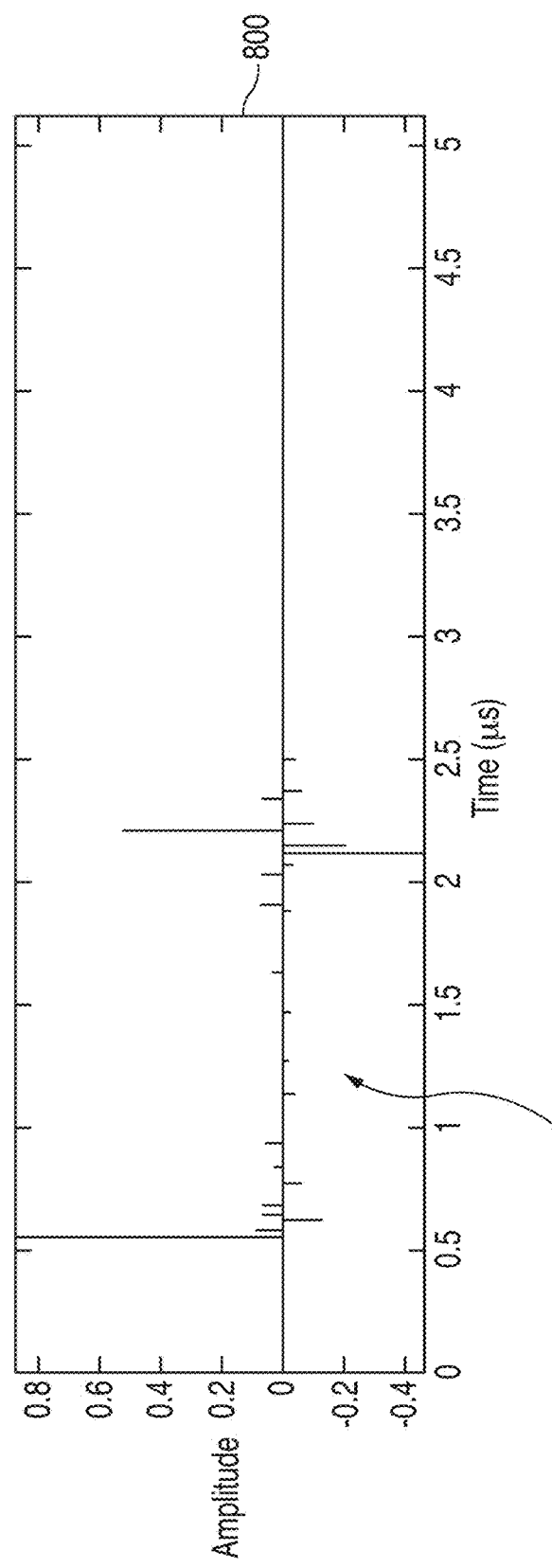
FIG. 8 is a plot that shows an echo pattern used in an aspect of the system and method of the present disclosure.

Next, at step 505 in flowchart 500 in FIG. 5, a starting set of echo patterns based on the stored library of echo patterns is chosen. The starting set of echoes is the subset of echo patterns that have a back wall attenuation within a certain predetermined range of the attenuation value selected at step 504. Then, at step 506, attenuation values are assigned to the remaining pixels within each sub-region that are within a predetermined percentage of the attenuation selected at step 504. For each pixel, the following process (step 507) is performed for the associated waveform:

1) The front-wall pulse portion of the waveform is extracted;

2) One of the starting echo patterns is selected (e.g., the pattern shown in FIG. 8), the location and amplitude of the echoes within the selected pattern are randomly perturbated, and the amplitude for the back wall pulse portion and any echoes after the back wall pulse portion are set to zero;

3) The extracted front-wall pulse is convolved with the modified echo pattern to create an interim ultrasound signal including the front-wall pulse and the internal signals;

4) The front-wall pulse is multiplied by the attenuation value selected in step 506 and the result is shifted in time to be a simulated back-wall pulse; and 5) The simulated back-wall pulse and preferably a predetermined level of random noise is added to the interim signal to generate a simulated waveform.

Figure 9:
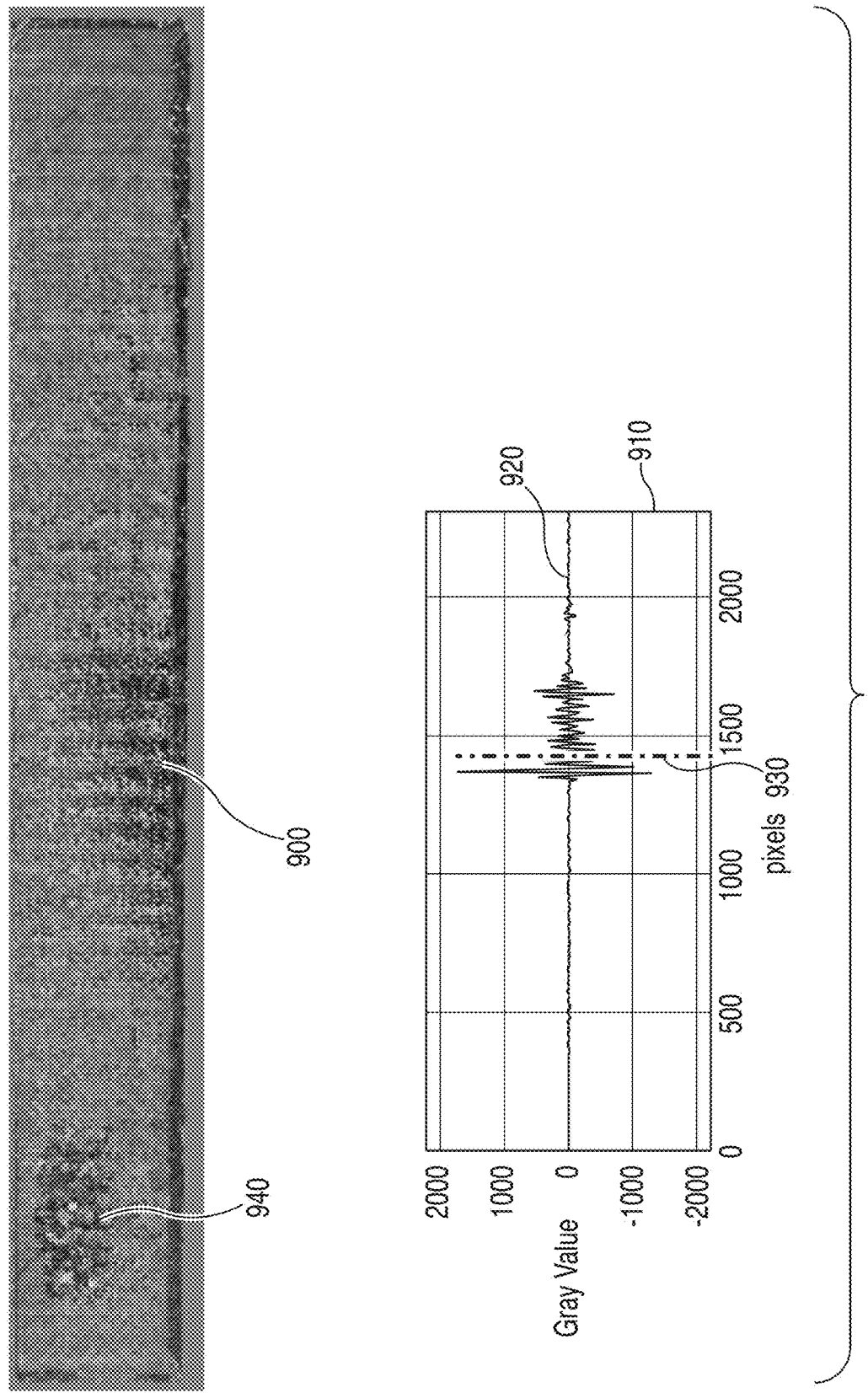
FIG. 9 shows a C-scan plot of an ultrasound test result for a non-porous composite coupon modified according to the present invention and an associated A-scan plot used to show a smoothing step according to an aspect of the system and method of the present disclosure.

After all waveforms in the region 610 have been modified, at step 508 in flowchart 500 in FIG. 5, a two-dimensional image smoothing is performed on the data at each time step. This is shown in FIG. 9, where the C-scan plot 900 includes a selected region 940 where porosity has been simulated. As shown by the related A-scan plot 910 of the ultrasound signal 920, a line 930 progresses along signal 920 as each smoothing step is performed.

Figure 10:
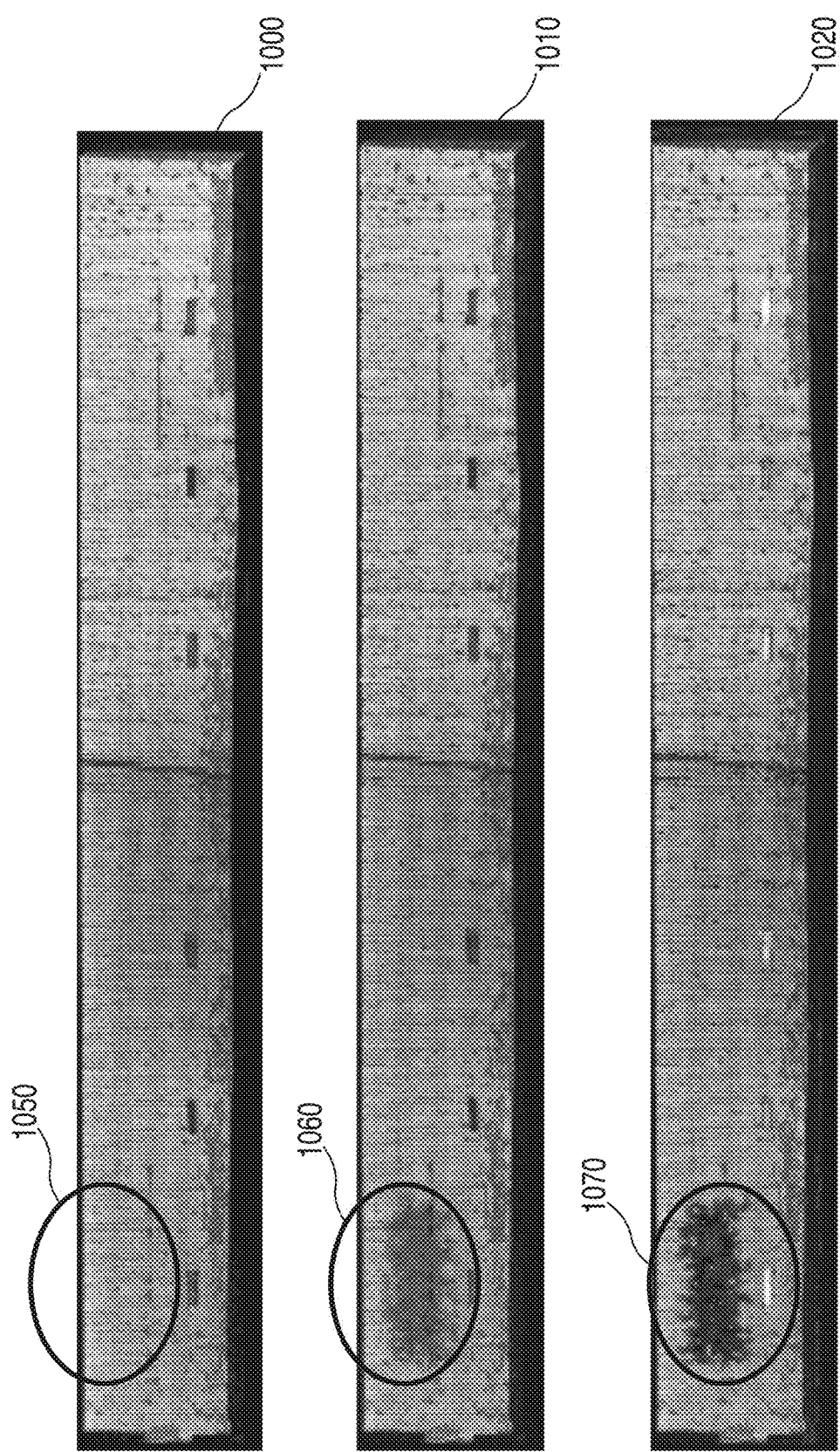
FIG. 10 shows a C-scan plot of an ultrasound test result for a non-porous composite coupon and two C-scan plots of simulated ultrasound test results for selected levels of porosity according aspects of the system and method of the present disclosure.

Referring now to FIG. 10, three C-scan plots 1000, 1010, 1020 are shown for varying levels of porosity in a composite. In particular, C-scan plot 1000 shows the original ultrasound test results for a composite coupon having no porosity, as evident by the region 1050 which is not significantly different from the remaining portions of C-scan plot 1000. Simulated C-scan plot 1010 shows the results of processing the ultrasound data used to plot C-scan plot 1000 by the steps of flowchart 500 in FIG. 5 to have a 1 percent porosity value. As evident, C-scan plot 1010 includes a region 1060 that is somewhat darker than the remaining portions of C-scan plot 1010. In addition, simulated C-scan plot 1020 shows the results of processing the ultrasound data used to plot C-scan plot 1000 by the steps of flowchart 500 in FIG. 5 to have a 5 percent porosity value. As evident, C-scan plot 1020 includes a region 1070 that is much darker than the remaining portions of C-scan plot 1020.

Figure 11:
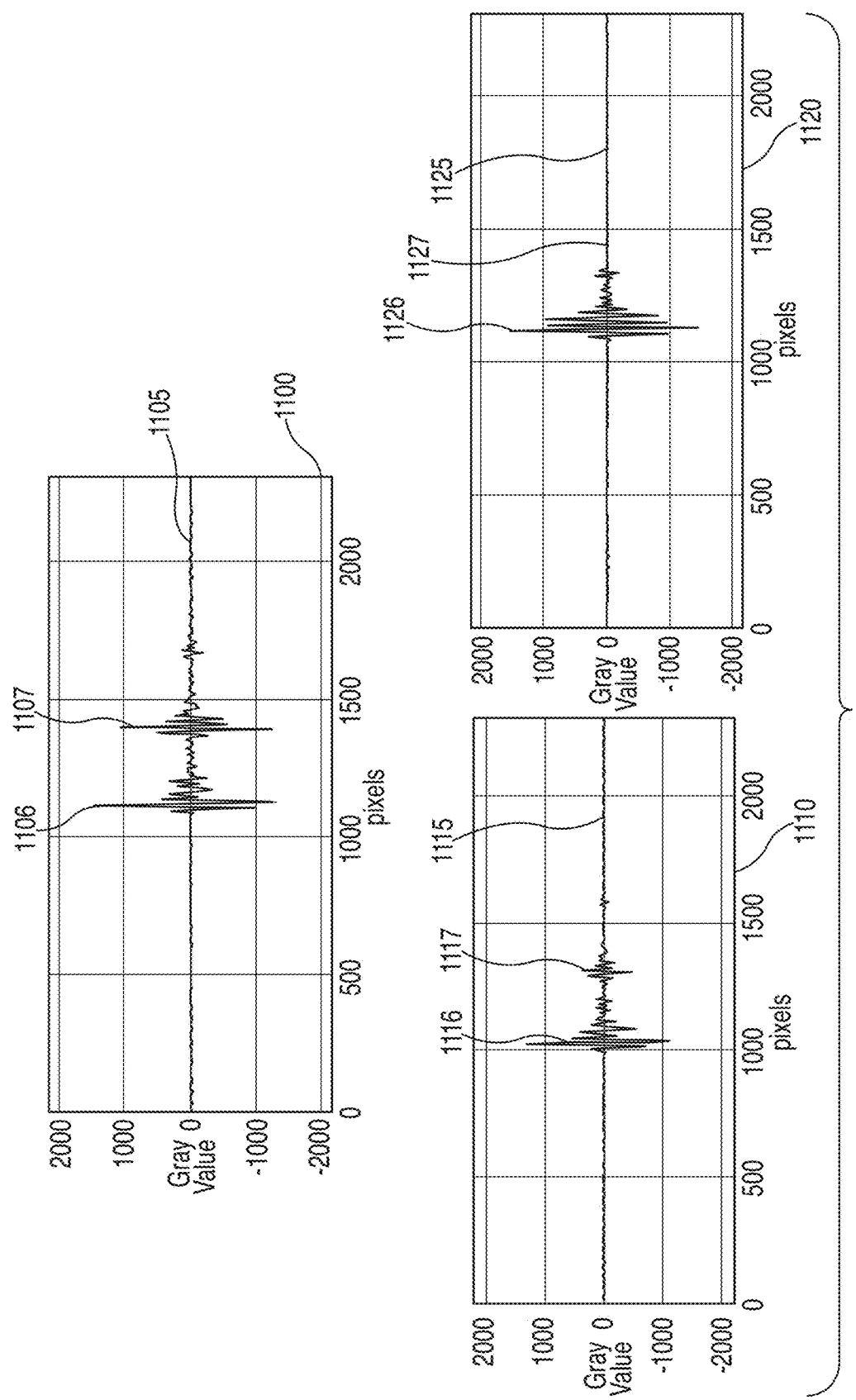
FIG. 11 shows a A-scan plot of an ultrasound test result for a non-porous composite coupon and two A-scan plots of simulated ultrasound test results for selected levels of porosity according aspects of the system and method of the present disclosure.

Referring now to FIG. 11, three A-scan plots 1100, 1110 and 1120 are shown for varying levels of porosity in a composite. A-scan plot 1100 shows the ultrasound test results for a composite coupon having no porosity. In particular, signal 1105 includes a front wall region 1106 that is comparable to a back wall region 1107, as expected in a composite coupon without porosity. However, simulated A-scan plot 1110 shows the results of processing the ultrasound data used to plot A-scan plot 1100 by the steps of flowchart 500 in FIG. 5 to have a 1 percent porosity value. As evident, simulated signal 1115 has a front wall region 1116 that is greater than the back wall region 1117. Next, simulated A-scan plot 1120 shows the results of processing the ultrasound data used to plot A-scan plot 1100 by the steps of flowchart 500 in FIG. 5 to have a 5 percent porosity value. As evident, simulated signal 1125 has a front wall region 1126 that is much greater than the back wall region 1127.

As discussed above, once the modified ultrasound test results are created for a particular level of porosity, such test results may be forwarded to a nondestructive testing system for use as a reference standard for that level of porosity. The above process for creating simulated ultrasound test results for a particular level of porosity may be repeated for many different levels of porosity, allowing the creation of a much greater number of porosity reference standards than previously available by use of actual composite coupons. For example, a complete set of porosity reference standards may be created by identifying the desired set of porosity levels for the set of porosity reference standards required for a nondestructive testing system, and the process above may be repeated for each porosity level in that desired set of porosity levels.

FIG. 12 is a block diagram of a non-destructive ultrasonic test system 1200 according to one illustrative and non-limiting implementation of the present disclosure.

The system 1200 includes an ultrasonic transducer 1280. The ultrasonic transducer 1280 is configured to produce an ultrasonic pulse (i.e., stimulus) of predetermined characteristics such as, for example, amplitude, wavelength, and so on. The ultrasonic transducer 1280 is further configured to detect any echoes that occur responsive to a stimulus pulse emitted by the ultrasonic transducer 1280. Such detected echoes are converted to corresponding electrical signals by the ultrasonic transducer 1280 and communicated to an apparatus 1210. The apparatus 1210 is configured to control the operation of the ultrasonic transducer 1280 and to receive echo signals there from. For purposes of non-limiting illustration, the ultrasonic transducer 1280 is depicted in FIG. 12 as being in operative contact with a composite test sample 1290, which may be a composite coupon used during the data modelling steps of FIG. 2 or during the data simulation steps of FIG. 5. As one of ordinary skill in the art will readily recognize, any type of material having a varying porosity may be tested using system 1200.

The apparatus 1210 in the system 1200 includes at least one processor 1220, memory (i.e., computer-accessible storage) 1230, and media 1240 that includes program code 1250. The at least one processor 1220 is configured to operate, at least in part, in accordance with the program code included on media 1240. In turn, the processor 1220 controls some, or all, of the operations and functions of the apparatus 1210 including, among other things, operation of and communication with the transducer 1280.

The memory 1230 is configured to be accessible to the processor 1220 such that data may be stored within and retrieved from the memory 1230. The memory 1230 can be defined by any suitable data (i.e., information) storage apparatus. Non-limiting examples of such memory 1230 include random access memory (RAM), non-volatile storage memory, an optical data storage device, a magnetic storage device (disk drive), electrically erasable programmable read only memory (EEPROM), etc. Other types of memory 1230 may also be used.

The media 1240, including the program code 1250, can be defined by any suitable storage such as, for non-limiting example, random access memory (RAM), non-volatile solid-state storage memory, one or more optical data storage units (e.g., CD-ROM, DVD, etc.), one or more magnetic storage units (i.e., floppy disks and/or hard disks, etc.), electrically erasable programmable read only memory (EEPROM) devices, etc. Other types of media 1250 may also be used. In any case, the media 1250 is defined by one or more tangible, computer-accessible storage entities, of one or more types and/or configurations, which include program code compatible with processor 1220.

The apparatus 1210 further includes other resources 1260 as required and/or desired for operations of the apparatus 1210. Non-limiting examples of such resources 1260 include digital-to-analog conversion (DAC) circuitry, analog-to-digital conversion (ADC) circuitry, a power supply or other energy source(s), a user interface, network communications resources, wireless communications resources, application specific integrated circuitry (ASIC), various electronic circuitry, and so on. One of skill in the instrumentation and related arts can appreciate that any suitable resources 1260 can be included so as to enable some number of normal operations and functions of the apparatus 1210. In at least one implementation, the apparatus 1210 is defined, at least in part, by a computer.

The system 1200 further includes an electronic display 1270. The display 1270 is coupled in signal communication with the apparatus 1210 so as to receive information (signals) there from and to graphically and/or textually present that information to a user. In at least one implementation, the display 1270 is configured to selectively provide A-scan and/or C-scan display of ultrasonic test information in accordance with the present disclosure. The display 1270 can also be configured to present other types and/or formats of information display.

The various elements of the system 1200 are individually and cooperatively configured to perform the methods of the present teachings. For non-limiting example, the system 1200 is configured to perform the methods depicted by FIGS. 2 and/or 5. Other suitable operations can also be performed by the system 1200. For example, system 1200 may be configured to perform the methods depicted in FIGS. 2 and 5 to generate simulated ultrasound test results for one or more predetermined levels of porosity, and then to compare the simulated results to actual test results for materials having unknown levels of porosity to identify the actual porosity levels in such materials. In any case, the system 1200 is illustrative and non-limiting with respect to the present teachings. For example, while only one ultrasonic transducer 1280 is depicted, it is to be understood that any suitable number of transducers 1280 may be used. In another example, and not by limitation, more than one electronic display 1270 can be included for simultaneous display of non-destructive testing data.

Although the present disclosure has been particularly shown and described with reference to the preferred embodiments and various aspects thereof, it will be appreciated by those of ordinary skill in the art that various changes and modifications may be made without departing from the spirit and scope of the disclosure. In particular, the present disclosure describes a system and method used to simulate ultrasound test data for composite materials having varying levels of porosity. As one of ordinary skill in the art will readily recognize, the system and method disclosed herein may be used on any material having varying levels of porosity. It is intended that the appended claims be interpreted as including the embodiments described herein, the alternatives mentioned above, and all equivalents thereto.

What is claimed is:

1. A method for generating simulated ultrasound test results having a selected level of porosity for a particular material under test, comprising the steps of:
    selecting a region of ultrasound test results for a coupon among a set of coupons of a selected material, the selected region within a region of porosity below a predetermined minimum threshold, the selected region for adding a predetermined amount of simulated porosity, the region of the ultrasound test results comprising a plurality of ultrasound waveforms;
    calculating a main attenuation distribution function based on an interpolation of two of a set of stored attenuation distribution functions for the set of coupons, one of the two stored attenuation distribution functions for a coupon in the set of coupons having a porosity less than the predetermined amount of simulated porosity and the other of the two stored attenuation distribution functions for a coupon in the set of coupons having a porosity greater than the predetermined amount of simulated porosity;
    assigning a main attenuation value to one portion of the selected region based on the main attenuation distribution function;
    modifying the ultrasound waveforms associated with the one portion of the selected region based on the main attenuation value and a selected one echo pattern of a library of echo patterns generated from ultrasound test data for the set of coupons;
    assigning attenuation values within a predetermined percentage of the main attenuation value to other portions of the selected region;
    modifying the ultrasound waveforms associated with the other portions of the selected region based on the attenuation values within the predetermined percentage of the main attenuation value and a selected one echo pattern of the library of echo patterns; and
    storing all of the modified ultrasound waveforms in a computer memory as simulated ultrasound waveforms for the predetermined amount of simulated porosity.

2. The method of claim 1, further comprising the step of performing a two-dimensional smoothing of all of the modified ultrasound waveforms prior to the storing step.

3. The method of claim 1, wherein the steps of modifying the ultrasound waveforms each comprise:
    extracting a front-wall pulse portion of each ultrasound waveform and storing the extracted front-wall pulse portion in the computer memory;
    modifying the selected echo pattern by setting a back-wall pulse portion in the selected echo pattern and any portion after the back-wall pulse portion in the selected echo pattern to zero;
    convolving the extracted front-wall pulse portion with the modified selected echo pattern to create an interim ultrasound signal;
    attenuating the stored extracted front-wall pulse portion by an associated attenuation value and time-shifting the attenuated stored extracted front-wall pulse portion to be a simulated back-wall pulse portion; and
    adding the simulated back-wall pulse portion to the interim ultrasound signal to create a simulated ultrasound waveform.

4. The method of claim 3, further comprising the step of:
    prior to the step of modifying the selected echo pattern, performing random perturbation of the location and amplitude of echoes in the selected echo pattern.

5. The method of claim 1, further comprising the step of forwarding the simulated ultrasound waveforms to a non-destructive testing system for use as a porosity reference standard for the selected level of porosity.

6. The method of claim 1, further comprising the step of dividing the selected region into a number of randomly-sized sub-regions, and wherein the step of calculating a main attenuation distribution function is performed for each sub-region, wherein the steps of assigning a main attenuation value and assigning attenuation values having values within a predetermined percentage of the main attenuation value are performed for each sub-region.

7. The method of claim 6, wherein the step of dividing the selected region into a number of randomly-sized sub-regions comprises selecting boxes of randomly-selected width and length to fill the selected region.

8. A system for generating simulated ultrasound test results having a selected level of porosity for a particular material under test, comprising:
  an ultrasound test system configured to perform ultrasound testing on a set of coupons for the particular material under test, each of the coupons having a different level of porosity and/or thickness, to generate ultrasound test data for each coupon; and
  a processor configured to fit a distribution function to a back wall attenuation signal for each coupon in the set of the coupons and to store the fitted distribution function in a memory as an attenuation distribution function, the back wall attenuation signal generated from the ultrasound test data for each coupon, the processor configured to create, from the ultrasound test data, a library of echo patterns for each coupon of unique porosity and thickness in the set of coupons and to store the library of echo patterns in the memory; the processor configured to select a region of ultrasound test results of a coupon having a region of zero porosity for adding a predetermined amount of simulated porosity, the processor configured to calculate a main attenuation distribution function based on an interpolation of two of the stored attenuation distribution functions, one of the two stored attenuation distribution functions for a coupon in the set of coupons having a porosity less than the predetermined amount of simulated porosity and the other of the two stored attenuation distribution functions for a coupon in the set of coupons having a porosity greater than the predetermined amount of simulated porosity, the processor configured to assign a main attenuation value to one portion of the selected region based on the main attenuation distribution function and to assign attenuation values within a predetermined percentage of the main attenuation value to other portions of the selected region, the processor configured to modify ultrasound waveforms associated with the one portion of the selected region based on the main attenuation value and a selected one echo pattern of the library of echo patterns, the processor configured to modify ultrasound waveforms associated with the other portions of the selected region based on the attenuation values within a predetermined percentage of the main attenuation value and a selected one echo pattern of the library of echo patterns, the processor configured to store all of the modified ultrasound waveforms in the memory as simulated ultrasound waveforms for the selected level of porosity.

9. The system of claim 8, wherein the processor is further configured to perform a two-dimensional smoothing of all of the modified ultrasound waveforms prior to the storing of the simulated ultrasound waveforms in the memory.

10. The system of claim 8, wherein the processor is further configured to modify the ultrasound waveforms associated with the one portion of the selected region and the ultrasound waveforms associated with the other portions of the selected region by extracting a front-wall pulse portion of each ultrasound waveform and storing the extracted front-wall pulse portion in the memory, modifying the selected echo pattern by setting a back-wall pulse portion in the selected echo pattern and any portion after the back-wall pulse portion in the selected echo pattern to zero, convolving the extracted front-wall pulse portion with the modified selected echo pattern to create an interim ultrasound signal, attenuating the stored front-wall pulse portion by an associated attenuation value and time-shifting the attenuated stored front-wall pulse portion to be a simulated back-wall pulse portion, and adding the simulated back-wall pulse portion to the interim ultrasound signal to create a simulated ultrasound waveform.

11. The system of claim 10, wherein the processor is further configured to, prior to the modifying of the selected echo pattern, perform random perturbation of the location and amplitude of echoes in the selected echo pattern.

12. The system of claim 8, wherein the processor is further configured to forward the simulated ultrasound waveforms to a nondestructive testing system for use as a porosity reference standard for the selected level of porosity.

13. The system of claim 8 wherein the processor is further configured to divide the selected region into a number of randomly-sized sub-regions, to calculate the main attenuation distribution function for each sub-region, and, for each sub-region, to assign the main attenuation value based on the calculated main attenuation distribution function for that sub-region and to assign the attenuation values within a predetermined percentage of the main attenuation value for that sub-region.

14. The system of claim 13, wherein the processor is further configured to divide the selected region into a number of randomly-sized sub-regions by selecting boxes of randomly-selected width and length to fill the selected region.

15. A method for generating a set of simulated ultrasound test results having predetermined levels of porosity for a particular material under test, comprising the steps of:
  selecting a region of ultrasound test results for a coupon among a set of coupons of a selected material, the selected region within a region of porosity below a predetermined minimum threshold, the selected region for adding a predetermined amount of simulated porosity, the region of the ultrasound test results comprising a plurality of ultrasound waveforms;
  for each of the predetermined levels of porosity:
    calculating a main attenuation distribution function based on an interpolation of two of a set of stored attenuation distribution functions for the set of coupons, one of the two stored attenuation distribution functions for a coupon in the set of coupons having a porosity less than a selected one of the predetermined levels of porosity and the other of the two stored attenuation distribution functions for a coupon in the set of coupons having a porosity greater than the selected one of the predetermined levels of porosity;
    assigning a main attenuation value to one portion of the selected region based on the main attenuation distribution function;
    modifying the ultrasound waveforms associated with the one portion of the selected region based on the main attenuation value and a selected one echo pattern of a library of echo patterns generated from ultrasound test data for the set of coupons;
    assigning attenuation values within the predetermined percentage of the main attenuation value to other portions of the selected region; and
    modifying the ultrasound waveforms associated with the other portions of the selected region based on the attenuation values within a predetermined percentage of the main attenuation value and a selected one echo pattern of the library of echo patterns; and
    storing all of the modified ultrasound waveforms in a computer memory as simulated ultrasound waveforms for the selected one of the predetermined levels of porosity.

16. The method of claim 15, further comprising the step of performing a two-dimensional smoothing of all of the modified ultrasound waveforms prior to the storing step.

17. The method of claim 15, wherein the steps of modifying the ultrasound waveforms each comprise:
   extracting a front-wall pulse portion of each ultrasound waveform and storing the extracted front-wall pulse portion in the memory;
   modifying the selected echo pattern by setting a back-wall pulse portion in the selected echo pattern and any portion after the back-wall pulse portion in the selected echo pattern to zero;
   convolving the extracted front-wall pulse portion with the modified selected echo pattern to create an interim ultrasound signal;
   attenuating the stored extracted front-wall pulse portion by an associated attenuation value and time-shifting the attenuated stored front-wall pulse portion to be a simulated back-wall pulse portion; and
   adding the simulated back-wall pulse portion to the interim ultrasound signal to create a simulated ultrasound waveform.

18. The method of claim 17, further comprising, for each of the predetermined levels of porosity, the step of:
   prior to the step of modifying the selected echo pattern, performing random perturbation of the location and amplitude of echoes in the selected echo pattern.

19. The method of claim 15, further comprising the step of forwarding all of the simulated ultrasound waveforms for each of the predetermined levels of porosity to a nondestructive testing system for use as porosity reference standards.

20. The method of claim 15, further comprising, for each of the predetermined levels of porosity, the step of dividing the selected region into a number of randomly-sized sub-regions, and wherein the step of calculating a main attenuation distribution function is performed for each sub-region for each of the predetermined levels of porosity, wherein the steps of assigning a main attenuation value and assigning attenuation values within a predetermined percentage of the main attenuation value are performed for each sub-region for each of the predetermined levels of porosity.

* * * * *